United States Patent
McGhee

(10) Patent No.: US 10,368,801 B2
(45) Date of Patent: Aug. 6, 2019

(54) AUTOMATIC MEDICATION DISPENSER WITH ELECTRONIC THERMOMETER

(71) Applicant: Shaviodla Shanta McGhee, Warner Robins, GA (US)

(72) Inventor: Shaviodla Shanta McGhee, Warner Robins, GA (US)

( * ) Notice: Subject to any disclaimer, the term of this patent is extended or adjusted under 35 U.S.C. 154(b) by 0 days.

(21) Appl. No.: 15/815,934

(22) Filed: Nov. 17, 2017

(65) Prior Publication Data

US 2018/0132785 A1 May 17, 2018

Related U.S. Application Data

(60) Provisional application No. 62/423,312, filed on Nov. 17, 2016.

(51) Int. Cl.

| | |
|---|---|
| *A61B 5/00* | (2006.01) |
| *A61B 7/00* | (2006.01) |
| *A61J 7/00* | (2006.01) |
| *G01K 13/00* | (2006.01) |
| *A61B 5/01* | (2006.01) |
| *G16H 50/20* | (2018.01) |
| *G16H 20/13* | (2018.01) |
| *A61J 7/04* | (2006.01) |
| *G06F 19/00* | (2018.01) |
| *A61J 1/06* | (2006.01) |

(52) U.S. Cl.
CPC .......... *A61B 5/4839* (2013.01); *A61B 5/0008* (2013.01); *A61B 5/01* (2013.01); *A61B 5/682* (2013.01); *A61J 7/0053* (2013.01); *A61J 7/0084* (2013.01); *G01K 13/002* (2013.01); *G16H 20/13* (2018.01); *G16H 50/20* (2018.01); *A61B 2505/07* (2013.01); *A61J 1/065* (2013.01); *A61J 7/0427* (2015.05); *A61J 2200/72* (2013.01); *G06F 19/3418* (2013.01); *G06F 19/3462* (2013.01)

(58) Field of Classification Search
CPC ....... A61B 5/0008; A61B 5/4839; A61B 5/01; A61B 5/682; A61B 2205/07; A61J 7/0084; A61J 7/0053; A61J 7/0427; A61J 2200/72; A61J 1/065; G01K 13/002; G16H 50/20; G16H 20/13; G06F 19/3462; G06F 19/3418
USPC .................................. 700/231–244
See application file for complete search history.

(56) References Cited

U.S. PATENT DOCUMENTS

| | | | |
|---|---|---|---|
| 3,977,401 A * | 8/1976 | Pike .................... | A61M 5/2053 604/144 |
| 4,534,343 A * | 8/1985 | Nowacki .......... | A61M 15/0086 128/200.23 |

(Continued)

*Primary Examiner* — Michael Collins
(74) *Attorney, Agent, or Firm* — Global Intellectual Property Agency, LLC; Daniel Boudwin

(57) ABSTRACT

An automatic medication dispenser with electronic thermometer. The automatic medication dispenser provides for the delivery of medication to a user upon detection of a body temperature above a predetermined amount. A housing can receive a cartridge having medication and dispense the medication through a valve, a tubular member, and a mouthpiece. An electronic thermometer detects the body temperature and also displays the body temperature on the housing. The body temperature determines if the valve allows for a dose of the medication to be administered.

17 Claims, 4 Drawing Sheets

(56) References Cited

U.S. PATENT DOCUMENTS

| | | | | |
|---|---|---|---|---|
| 4,796,614 | A * | 1/1989 | Nowacki | A61M 15/0086 128/200.14 |
| 5,435,282 | A * | 7/1995 | Haber | A61M 15/0065 128/200.14 |
| 5,611,622 | A | 3/1997 | Wang | |
| 5,809,997 | A * | 9/1998 | Wolf | A61M 15/009 128/200.23 |
| 5,957,125 | A * | 9/1999 | Sagstetter | A61M 15/009 128/200.23 |
| 8,328,420 | B2 * | 12/2012 | Abreu | A61B 5/0008 374/163 |
| 8,751,039 | B1 * | 6/2014 | Macoviak | A61J 7/0076 700/244 |
| 8,807,131 | B1 * | 8/2014 | Tunnell | A61M 16/0051 128/200.23 |
| 2003/0120384 | A1 | 6/2003 | Haitin et al. | |
| 2005/0188853 | A1 | 9/2005 | Scannell | |
| 2006/0231109 | A1 * | 10/2006 | Howell | A61B 5/6887 128/898 |
| 2012/0316405 | A1 | 12/2012 | Taylor | |
| 2013/0008436 | A1 * | 1/2013 | Von Hollen | A61M 15/0086 128/200.14 |
| 2015/0094609 | A1 * | 4/2015 | Jacobson | A61F 5/08 600/549 |

\* cited by examiner

AUTOMATIC MEDICATION DISPENSER WITH ELECTRONIC THERMOMETER

CROSS REFERENCE TO RELATED APPLICATIONS

This application claims the benefit of U.S. Provisional Application No. 62/423,312 filed on Nov. 17, 2016. The above identified patent application is incorporated by reference in its entirety to provide continuity of disclosure.

BACKGROUND OF THE INVENTION

This invention relates to an automatic medication dispenser with an electronic thermometer. It can be tremendously difficult for a parent, guardian or healthcare provider to take the temperature of an infant, child or otherwise uncooperative patient in need of care. It is also difficult to provide such patients with medicine if their temperature indicates that they may be sick, whether because of the unpleasant taste of the medicine or the requirement to sit still while taking medicine Currently available devices only focus on either taking the temperature of a patient or on determining the proper dosage of medicine for a patient. There is no currently available device that both records the temperature of a patient while simultaneously releasing medicine if a certain temperature is recorded. By solving this problem, healthcare efficiency can be improved in both home and professional medical settings, medicine can more easily be given to an infant, an unruly child or an uncooperative patient, and the risk of medicine being spilled or wasted can be reduced.

SUMMARY OF THE INVENTION

In view of the foregoing disadvantages inherent in the known types of electronic thermometers or medication delivery devices now present n the known art, the present invention provides an automatic medication dispenser with an electronic thermometer wherein the same can be utilized for providing convenience for the user when taking the temperature of an infant, child or uncooperative patient and simultaneously providing medicine to that patient or the user.

The present system comprises a housing that defines a cavity with an upper compartment. The upper compartment has an open upper end configured to removably receive a cartridge containing a medication. There is a valve disposed within the cavity which is configured to releasably couple with the cartridge. The valve controls fluid communication between the coupled cartridge and a tubular member. The tubular member is in fluid communication with a mouthpiece. The mouthpiece is a hollow conical member configured to dispense the medication. An actuator is operably connected to the valve. Activation of the actuator discharges a dose of the medication from the coupled cartridge. There is an electronic thermometer mounted to the mouthpiece that is also operably coupled to the actuator. When the electronic thermometer detects a body temperature above a first predetermined temperature, the actuator is activated.

One object of the present invention is to provide an L-shaped housing that is easily hand-held and operable with a single hand.

Another object of the present invention is to provide a temperature display on an external surface of the housing. The display is coupled to the electronic thermometer. By displaying the temperature that is gathered by the thermometer, the user would have knowledge of their recorded temperature.

Another object of the present invention is to provide a mechanism by which the user can activate and deactivate the device. This would give the user additional control over the automatic medication dispenser and would allow them to conserve the power supply of the automatic medication dispenser.

Another object of the present invention is to provide a mouthpiece that is shaped to dispense medication into the mouth of a patient. Such shaping would make the device more comfortable for a user and would assist in the control of the flow of medication.

Another object of the present invention is to provide a mouthpiece that is made of a soft, rubber material that would make the automatic medication dispenser more comfortable for a user.

Another way that the mouthpiece can be arranged is in a manner that would cover the mouth of a user, assisting in the delivery of medication from the automatic medication dispenser.

In one embodiment of the invention, the tubular member is coupled to the cartridge by penetration of a first end of the tubular member into an internal cavity of the cartridge. This manner would ensure that the medication is able to travel into the tubular member and that the medication can be properly dispensed from the automatic medication dispenser.

One object of the invention is that the automatic medication dispenser is run by a logic that causes the automatic medication dispenser system to perform a method where the body temperature of the user is detected. Upon the detection of a body temperature above a predetermined temperature, the actuator is activated, and the valve causes a discharge of a dose of the medication. On the other hand, if the detected body temperature is equal or below a predetermined temperature, the actuator is inhibited, and the automatic medication dispenser is incapable of discharging any medication. This will enable a more efficient process of providing medication to a user that may have a fever or other ailment.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
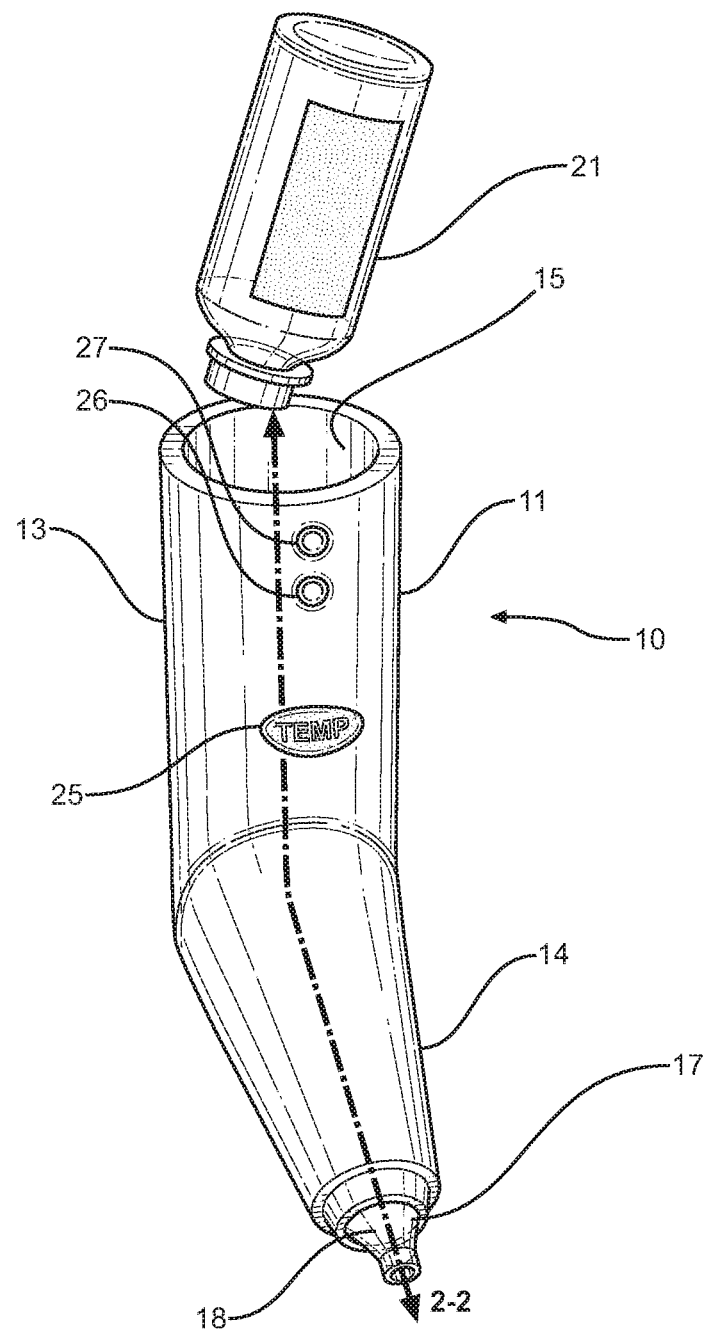
FIG. 1 shows a perspective view of the automatic medication dispenser.

Reference is made herein to the attached drawings. Like reference numerals are used throughout the drawings to depict like or similar elements of the automatic medication dispenser. The figures are intended for representative purposes only and should not be considered to be limiting in any respect.

Figure 2:
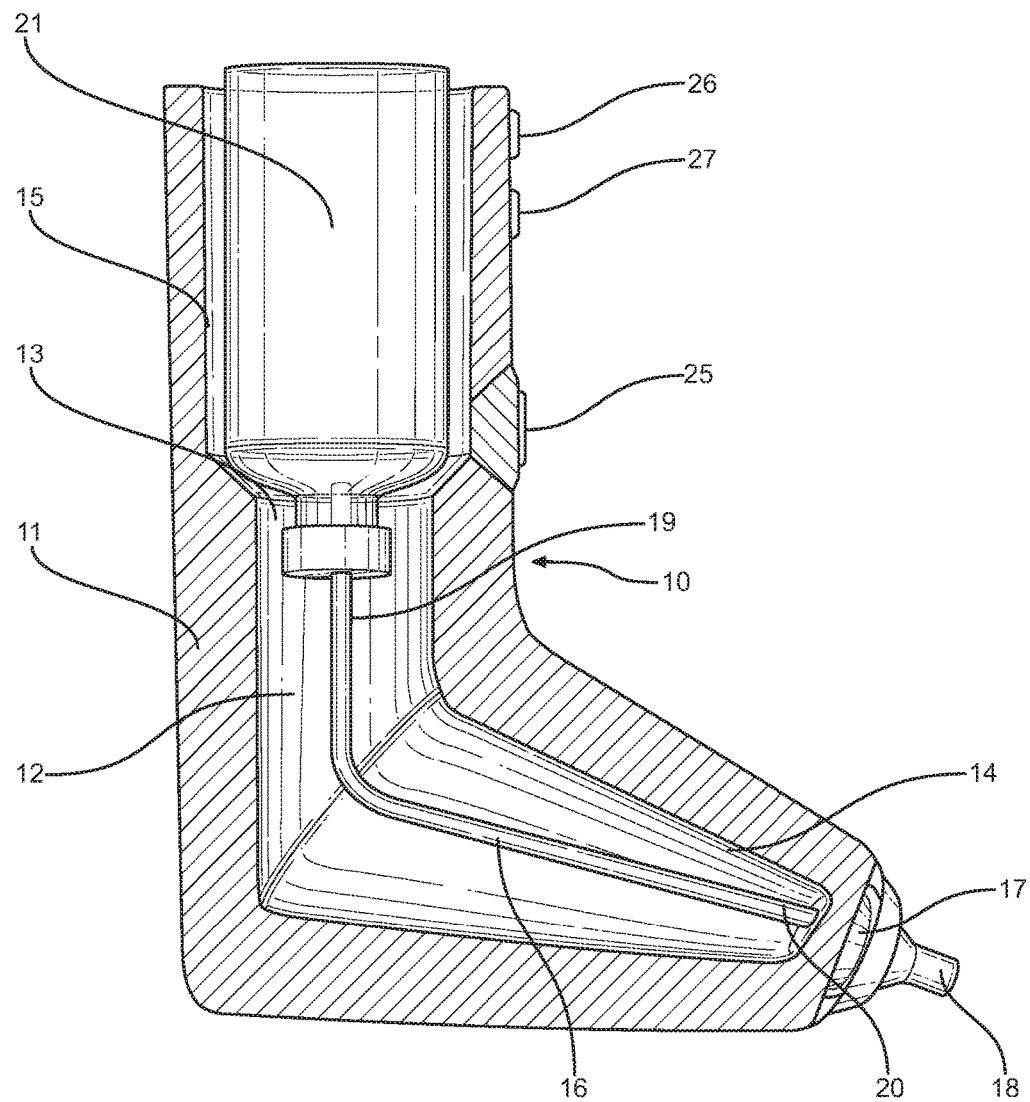
FIG. 2 shows a cross-sectional view of the automatic medication dispenser taken along line 2-2 of FIG. 1.

Referring now to FIGS. 1-2, there is shown a perspective view of the automatic medication dispenser and a cross-sectional view along line 2-2 thereof, respectively. The automatic medication dispenser 10 includes a housing 11 that defines a cavity 12. The housing has an upper compartment 13 with an open upper end 15. The upper compartment 13 is configured to removably receive a cartridge 21. The cartridge 21 contains a medication therein. The medication in the cartridge 21 may be any medication which would be desired to use in the treatment of a patient with a fever or other ailment.

In one embodiment, the housing 11 may be an L-shaped tubular housing, as shown in the figures, that defines both an upper compartment 13 and a lower compartment 14. An L-shaped tubular housing would be desirable because it would allow the user to grasp the automatic medication dispenser 10 more comfortably and more securely. Alternatively, the housing 11 may be cylindrical, spherical and the like, and sized to fit comfortably in the hands of a user. Further, the housing 11 may be made of any material that would be suitable for a hand-held electronic device.

In the shown embodiment, the lower compartment 14 has a lower open end 17. A tubular member 16 is disposed in the cavity 12 and has a first end 19 and a second end 20. A valve 22 is configured to releasably couple with the cartridge 21 that controls fluid communication between the coupled cartridge 21 and the tubular member 16. The valve 22 may be located on the first end 19 or on the second end 20 of the tubular member 16. In one embodiment, the first end 19 of the tubular member 16 may connect to the cartridge 21 through the penetration of the first end 19 of the tubular member 16 into the cartridge 21 in a way that would allow the medication in the cartridge 21 to flow into the tubular member 16.

Referring specifically to FIG. 2, the tubular member 16 is disposed in the cavity 12 and is in fluid communication with a mouthpiece 18. The tubular member 16 provides for the delivery of the medication from the coupled cartridge 21 to the mouthpiece 18. The tubular member 16 may have one or more joints and may contour the shape of the cavity 12 in a way that promotes the flow of medication through the automatic medication dispenser 10. Additionally, the tubular member 16 may be rigid or flexible and may be made of any material suitable for the delivery of medicine. The tubular member 16 may be arranged in a manner to house a specific volume of medicine.

The mouthpiece 18 may be a hollow conical member having a base and a tip. The base may contain a connection mechanism to connect the mouthpiece 18 to the housing 11. In the embodiment having an L-shaped housing member, the base may connect the mouthpiece 18 to the housing 11 at the lower open end 17. In one embodiment, the tip contains an aperture configured to allow medicine to be released from the automatic medication dispenser 10 into an oral cavity of the user. The mouthpiece 18 may be made of any suitable material for delivering medicine into the oral cavity of the user. In one embodiment, the mouthpiece 18 is made of a soft rubber material. This embodiment would increase the comfort of the mouthpiece 18 in the oral cavity of a user. Additionally, the mouthpiece 18 may also be a soft rubber nipple attachment for use with infants or children. Further, the mouthpiece 18 may be disposable to prevent the contamination of the automatic medication dispenser 10 and enable a user to use the automatic medication dispenser 10 on multiple patients safely in a short time. In another embodiment, the mouthpiece 18 may be configured to wholly cover the mouth of a user.

In one embodiment, the automatic medication dispenser 10 includes a power control unit configured to allow the user to activate and deactivate the automatic medication dispenser 10. In one embodiment, the power control unit is comprised of an "on" button 26 and an "off" button 27. In another embodiment, the power control unit is an external switch that has an "on" position and an "off" position.

In one embodiment, the automatic medication dispenser 10 has a temperature display 25 located on an external surface of the housing 11. The temperature display 25 is operably coupled to the electronic thermometer 24 and is programmed to display the temperature that is gathered by the electronic thermometer 24.

Figure 3:
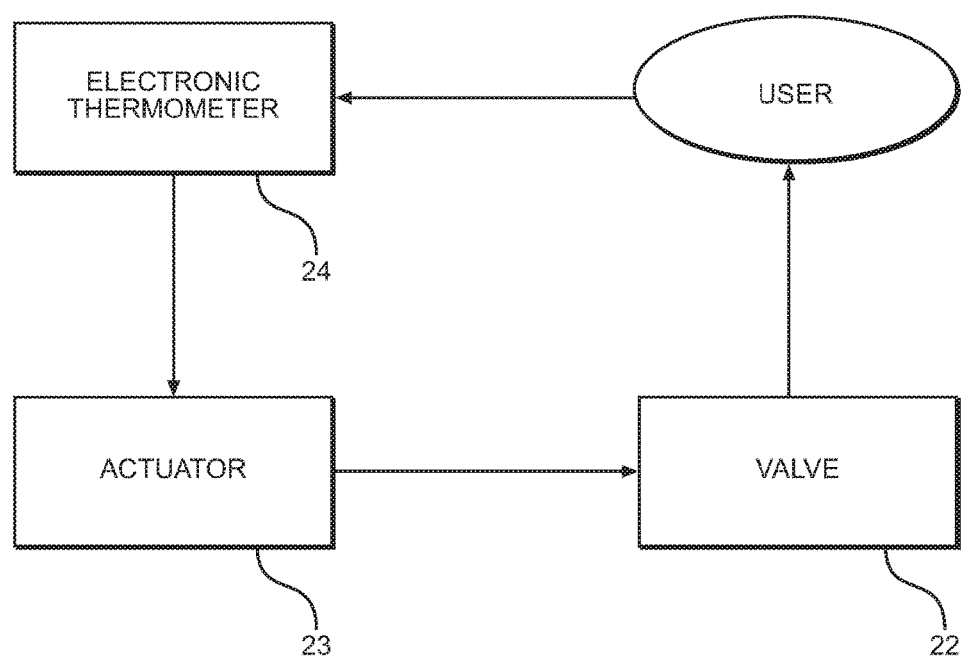
FIG. 3 shows a block diagram demonstrating the function of the actuator, the valve, and the electric thermometer.

Referring now to FIG. 3, there is shown a block diagram that demonstrates the relationships and functions of the electrical components of the automatic medication dispenser 10. An electronic thermometer 24 and the valve 22 are operably coupled to an actuator 23. The electronic thermometer 24 may be disposed on the device from which the body temperature of the user may be measured. In one embodiment, the electronic thermometer 24 is embedded in the mouthpiece 18.

The electronic thermometer 24, when placed into the oral cavity of the user will record the body temperature of the user. Upon detection of the body temperature above a predetermined temperature, the actuator 23 is activated, causing a discharge of a dose of the medication from the coupled cartridge 21 to be released through the valve 22 and into the oral cavity of the user. Upon the detection of the body temperature equal to or below a predetermined temperature, the actuator 23 is not activated and the valve 22 will not be opened.

Figure 4:
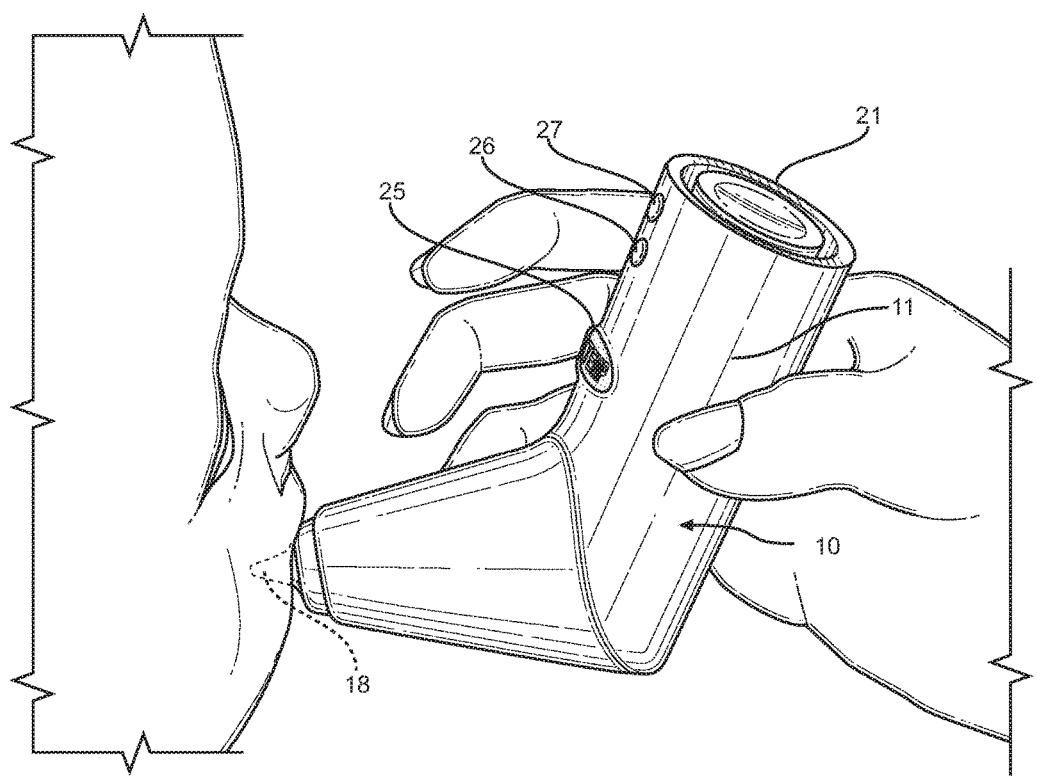
FIG. 4 shows a perspective view of the automatic medication dispenser in use.

Referring now to FIG. 4, there is shown a perspective view of how the cartridge 21 is inserted into the automatic medication dispenser. The cartridge may be comprised of a storage unit, a head unit attached to the storage unit and a puncturable lid covering the head unit. Under this embodiment, the user will insert the medicine bottle into the automatic medication dispenser by the head unit. The first end 19 of the tubular member 16 will puncture the lid of the cartridge 21. The medication housed in the cartridge 21 will enter the tubular member 16 through the first end 19 and be transported out of the mouthpiece 18 upon the action of the actuator 23 upon the valve 22.

The cartridge 21 can also be removed from the automatic medication dispenser. The user will grasp the storage unit of the cartridge 21 and lift upward relative to the housing 11. It may be desirable for the user to remove the cartridge 21 from the automatic medication dispenser when the medicine in the cartridge 21 has been exhausted or the user desires to treat a patient with a different medicine than the medicine in the cartridge 21. The first end 19 of the tubular member 16 may be capable of being cleaned to prevent the contamination of the medicine in the cartridge 21 from residue of a previously used cartridge.

To fully operate the automatic medication dispenser, the present invention is turned on by engaging the activation mechanism. A cartridge 21 is inserted into the automatic medication dispenser. The mouthpiece 18 of the automatic medication dispenser is placed into the oral cavity of the user. The electronic thermometer 24 records the temperature of the user. The recorded temperature of the user will be displayed on the temperature display 25. If the recorded temperature of the patient reaches a designated temperature range, the actuator 23 will act upon the valve 22. The valve 22 will release the medicine from the tubular member 16 into the mouthpiece 18. The medicine will flow into the mouthpiece 18 and out of the aperture into the oral cavity of the user. The present invention is deactivated through action upon the deactivation mechanism. The cartridge 21 can be removed from the automatic medication dispenser.

It is therefore submitted that the instant invention has been shown and described in various embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An automatic medication dispenser comprising:
   a housing defining a cavity forming an upper compartment, wherein the upper compartment includes an open upper end configured to removably receive a cartridge containing a medication therein;
   a valve disposed within the cavity, the valve configured to releasably couple with the cartridge;
   wherein the valve controls fluid communication between the coupled cartridge and a tubular member;
   the tubular member in fluid communication with a mouthpiece configured to dispense the medication therethrough;
   an actuator operably connected to the valve, wherein activation of the actuator discharges a dose of the medication from the coupled cartridge;
   an electronic thermometer configured to detect a body temperature, the electronic thermometer mounted to the mouthpiece;
   the electronic thermometer operably coupled to the actuator, wherein the actuator activates upon detection of the body temperature above a first predetermined temperature.

2. The automatic medication dispenser of claim 1, wherein the housing is L-shaped and defines a lower compartment that houses the tubular member.

3. The automatic medication dispenser of claim 1, further comprising a temperature display on an external surface of the housing, the temperature display operably coupled to the electronic thermometer, wherein the temperature display is configured to display the temperature as gathered by the electronic thermometer.

4. The automatic medication dispenser of claim 1, further comprising a power control unit configured to activate and deactivate the device.

5. The automatic medication dispenser of claim 1, wherein the mouthpiece comprises a hollow conical member sized to dispense medication into the mouth of a user.

6. The automatic medication dispenser of claim 1, wherein the mouthpiece is made of a soft rubber material.

7. The automatic medication dispenser of claim 1, wherein the mouthpiece is sized to cover the mouth of a user.

8. The automatic medication dispenser of claim 1, wherein the tubular member is coupled to the cartridge by penetration of a first end of the tubular member into an internal cavity of the cartridge.

9. An automatic medication dispenser system comprising:
   a housing defining a cavity forming an upper compartment, wherein the upper compartment includes an open upper end configured to removably receive a cartridge containing a medication therein;
   a valve disposed within the cavity, the valve configured to releasably couple with the cartridge;
   wherein the valve controls fluid communication between the coupled cartridge and a tubular member;
   the tubular member in fluid communication with a mouthpiece, the mouthpiece comprising a hollow conical member configured to dispense the medication therethrough;
   a logic that is at least partially stored in a non-transitory computer readable medium and that, when executed at least in part by a processor, causes the automatic medication dispenser system to perform a method, the method comprising:
      detecting a body temperature of a user via an electronic thermometer mounted to the mouth piece;
      upon detection of the body temperature above a predetermined temperature, activating an actuator operably connected to the valve causing a discharge of a dose of the medication from the coupled cartridge;
      upon detection of the body temperature equal or below a predetermined temperature, inhibiting the actuator from discharging the dose of the medication from the coupled cartridge.

10. The automatic medication dispenser system of claim 9, wherein the housing is L-shaped and defines a lower compartment that houses the tubular member.

11. The automatic medication dispenser system of claim 9, further comprising a temperature display on an external surface of the housing, the temperature display operably coupled to the electronic thermometer, wherein the temperature display is configured to display the temperature as gathered by the electronic thermometer.

12. The automatic medication dispenser system of claim 9, further comprising a power control unit configured to activate and deactivate the device.

13. The automatic medication dispenser system of claim 9, wherein the mouthpiece comprises a hollow conical member sized to dispense medication into the mouth of a user.

14. The automatic medication dispenser system of claim 9, wherein the mouthpiece is made of a soft rubber material.

15. The automatic medication dispenser system of claim 9, wherein the mouthpiece is sized to cover the mouth of a user.

16. The automatic medication dispenser system of claim 9, wherein the tubular member is coupled to the cartridge by penetration of a first end of the tubular member into an internal cavity of the cartridge.

17. An automatic medication dispenser comprising:
   a housing defining a cavity and an open upper end;
   a valve disposed within the cavity, the valve configured to releasably couple with a cartridge containing a substance;
   wherein the valve controls fluid communication between the cartridge and a channel;
   the channel in fluid communication with a mouthpiece;

the mouthpiece configured to dispense the substance therethrough;
an actuator operably connected to the valve, wherein activation of the actuator discharges the substance from the cartridge;
a thermometer mounted to the mouthpiece.

\* \* \* \* \*